(12) United States Patent
Janssen et al.

(10) Patent No.: US 11,351,389 B2
(45) Date of Patent: Jun. 7, 2022

(54) CHARGING-INDUCED IMPLANT OPERATION

(71) Applicants: Jan Raymond Janssen, St. Ives (AU); Koen Van den Heuvel, Hove (BE); Richard Bruce Murphy, Kirribili (AU)

(72) Inventors: Jan Raymond Janssen, St. Ives (AU); Koen Van den Heuvel, Hove (BE); Richard Bruce Murphy, Kirribili (AU)

(73) Assignee: Cochlear Limited, Macquarie University (AU)

( * ) Notice: Subject to any disclaimer, the term of this patent is extended or adjusted under 35 U.S.C. 154(b) by 192 days.

(21) Appl. No.: 16/722,515

(22) Filed: Dec. 20, 2019

(65) Prior Publication Data

US 2020/0197709 A1    Jun. 25, 2020

Related U.S. Application Data

(63) Continuation of application No. 15/678,379, filed on Aug. 16, 2017, now Pat. No. 10,525,271.

(51) Int. Cl.

| | | |
|---|---|---|
| *A61N 1/378* | (2006.01) | |
| *H02J 7/02* | (2016.01) | |
| *A61N 1/36* | (2006.01) | |
| *H04R 25/00* | (2006.01) | |
| *H02J 50/10* | (2016.01) | |

(Continued)

(52) U.S. Cl.
CPC ........... *A61N 1/3787* (2013.01); *A61N 1/361* (2013.01); *A61N 1/36038* (2017.08); *A61N 1/36142* (2013.01); *H02J 7/025* (2013.01); *H02J 50/10* (2016.02); *H02J 50/80* (2016.02); *H04R 25/305* (2013.01); *H04R 25/505* (2013.01); *A61B 5/0255* (2013.01); *A61B 5/6817* (2013.01); *A61N 1/0541* (2013.01); *A61N 1/36139* (2013.01); *H02J 7/00034* (2020.01); *H02J 7/0071* (2020.01); *H04R 25/55* (2013.01); *H04R 25/554* (2013.01); *H04R 2225/31* (2013.01); *H04R 2225/33* (2013.01); *H04R 2225/41* (2013.01); *H04R 2225/61* (2013.01); *H04R 2225/67* (2013.01); *H04R 2460/03* (2013.01)

(58) Field of Classification Search
CPC ... A61N 1/3787; A61N 1/36038; H02J 50/10; H04R 25/305
USPC .......................................................... 607/57
See application file for complete search history.

(56) References Cited

U.S. PATENT DOCUMENTS 6,210,321 B1 *   4/2001   Di Mino .................. A61F 11/00
                                                           600/28
6,697,674 B2    2/2004   Leysieffer
(Continued)

*Primary Examiner* — Amanda K Hulbert
*Assistant Examiner* — Philip C Edwards
(74) *Attorney, Agent, or Firm* — Edell, Shapiro & Finnan, LLC

(57) ABSTRACT

Presented herein are techniques for initiating a night-time mode of operation in an implantable hearing prosthesis in response to detection of night-time recharging operations. More specifically, an implantable hearing prosthesis comprises a rechargeable battery that is configured to be recharged via an external night-time charging device, such as a pillow charger. The implantable hearing prosthesis is configured to detect inductive charging of the rechargeable battery by the external night-time charging device. In response, the implantable hearing prosthesis is switched to a night-time mode of operation.

25 Claims, 6 Drawing Sheets

(51) Int. Cl.
*H02J 50/80* (2016.01)
*A61N 1/05* (2006.01)
*A61B 5/0255* (2006.01)
*A61B 5/00* (2006.01)
*H02J 7/00* (2006.01)

(56) References Cited

U.S. PATENT DOCUMENTS

2012/0214418 A1* 8/2012 Lee .................. H02J 50/12
 455/41.2
2017/0179749 A1* 6/2017 Mansour ............ H02J 50/10

* cited by examiner

CHARGING-INDUCED IMPLANT OPERATION

CROSS-REFERENCE TO RELATED APPLICATIONS

This application is a continuation of U.S. application Ser. No. 15/678,379, filed on Aug. 16, 2017, the entire contents of which are incorporated by reference.

BACKGROUND

Field of the Invention

The present invention relates generally to operations of an implantable medical device that are induced by the initiation of implant charging.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or are employed to investigate, replace or modify the anatomy or a physiological process. Many of these functional components utilize power and/or data received from external components that are part of, or operate in conjunction with, the implantable medical device.

SUMMARY

In one aspect a method performed at an implantable hearing prosthesis comprising a rechargeable battery is provided. The method comprises: detecting inductive charging of the rechargeable battery by an external night-time charging device; and in response to detecting the inductive charging of the rechargeable battery, switching the implantable hearing prosthesis to a night-time mode of operation.

In another aspect an implantable hearing prosthesis is provided. The implantable hearing prosthesis comprises: an implantable coil configured to be inductively coupled to an external coil of an external night-time charging device; an implantable rechargeable battery; and an implant controller configured to detect a charging cycle in which the rechargeable battery is charged using signals received from the external night-time charging device, and, when the rechargeable battery is charged using signals received from the external night-time charging device, initiate a night-time mode of operation for the implantable hearing prosthesis.

BRIEF DESCRIPTION OF THE DRAWINGS

Embodiments of the present invention are described herein in conjunction with the accompanying drawings, in which.

DETAILED DESCRIPTION

Presented herein are techniques for initiating a night-time mode of operation in an implantable hearing prosthesis in response to detection of night-time recharging operations. More specifically, an implantable hearing prosthesis comprises a rechargeable battery that is configured to be recharged via an external night-time charging device, such as a pillow charger. The implantable hearing prosthesis is configured to detect inductive charging of the rechargeable battery by the external night-time charging device. In response, the implantable hearing prosthesis is switched to a night-time mode of operation.

Merely for ease of illustration, the techniques presented herein are primarily described with reference to one type of implantable medical device, namely a cochlear implant. It is to be appreciated that the techniques presented herein may be implemented by any other partially or fully implantable medical device now known or later developed, including other implantable hearing prostheses, such as auditory brainstem stimulators, electro-acoustic hearing prostheses, bimodal hearing prostheses, etc., and/or other types of medical devices, such as pain relief implants, pacemakers, etc.

Figure 1:
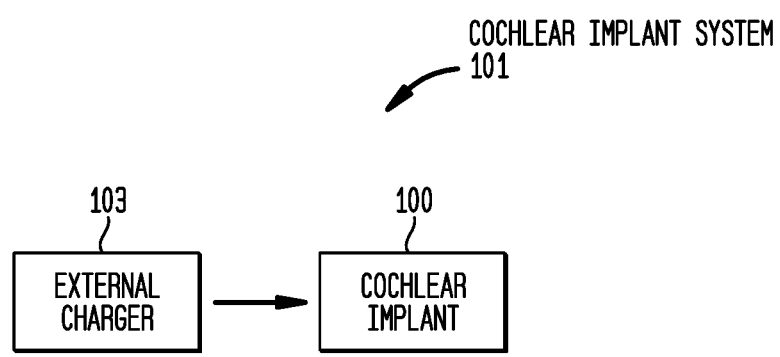
FIG. 1 is a block diagram illustrating a cochlear implant system, in accordance with certain embodiments presented herein.

FIG. 1 is a block diagram of an exemplary system 101 that includes a cochlear implant 100 in accordance with embodiments presented 100 and an external night-time charging device 103. The night-time charger 103 may have a number of different forms, such as a pillow charger, charging mat, neck pillow, etc., but is generally a non-battery powered device (i.e., a device connected to mains electric power) configured to supply charging power to an implantable medical device while the recipient of the medical device sleeps. For ease of description, embodiments are primarily described herein with reference to the night-time charger 103 as a pillow charger.

As described below, the cochlear implant 100 comprises a rechargeable battery (not shown in FIG. 1) that is configured to be recharged using power signals received from the pillow charger 103 via an inductive radio frequency (RF) link. Also as described below, the pillow charger 103 is a device that includes one or more coil antennas that emits a magnetic field and which is arranged to be positioned in proximity to a recipient's head while he or she sleeps. Each of the coil antennas are formed by a plurality of "wire loops" or "windings" of electrical conductors. As described further below, the cochlear implant 100 is configured to detect inductive charging of the rechargeable battery by the pillow charger 103 and, in response, switch the cochlear implant 100 to a night-time mode of operation.

Figure 2A:
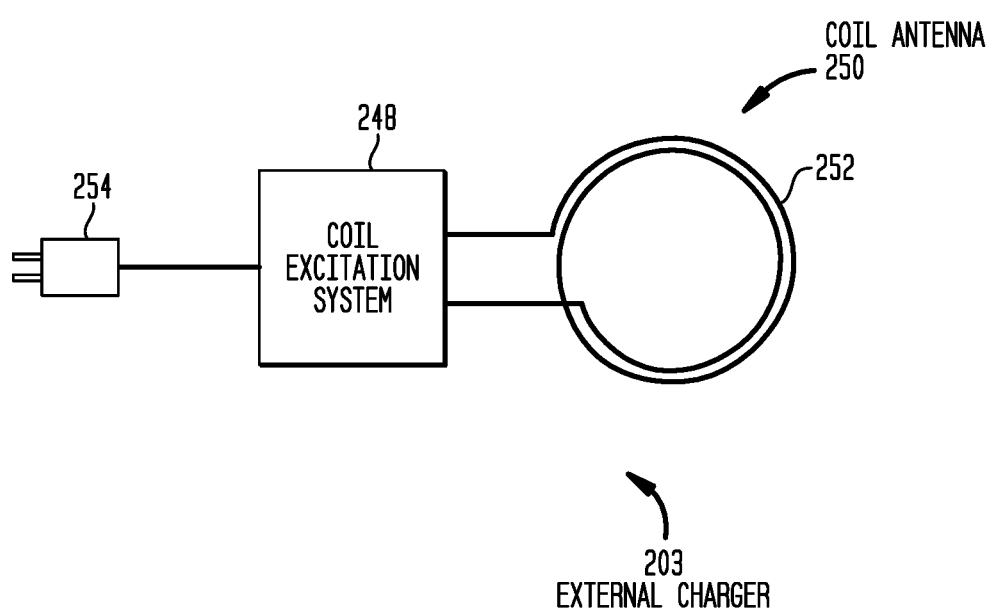
FIG. 2A is a schematic block diagram of a pillow charger, in accordance with certain embodiments presented herein.
Figure 2B:
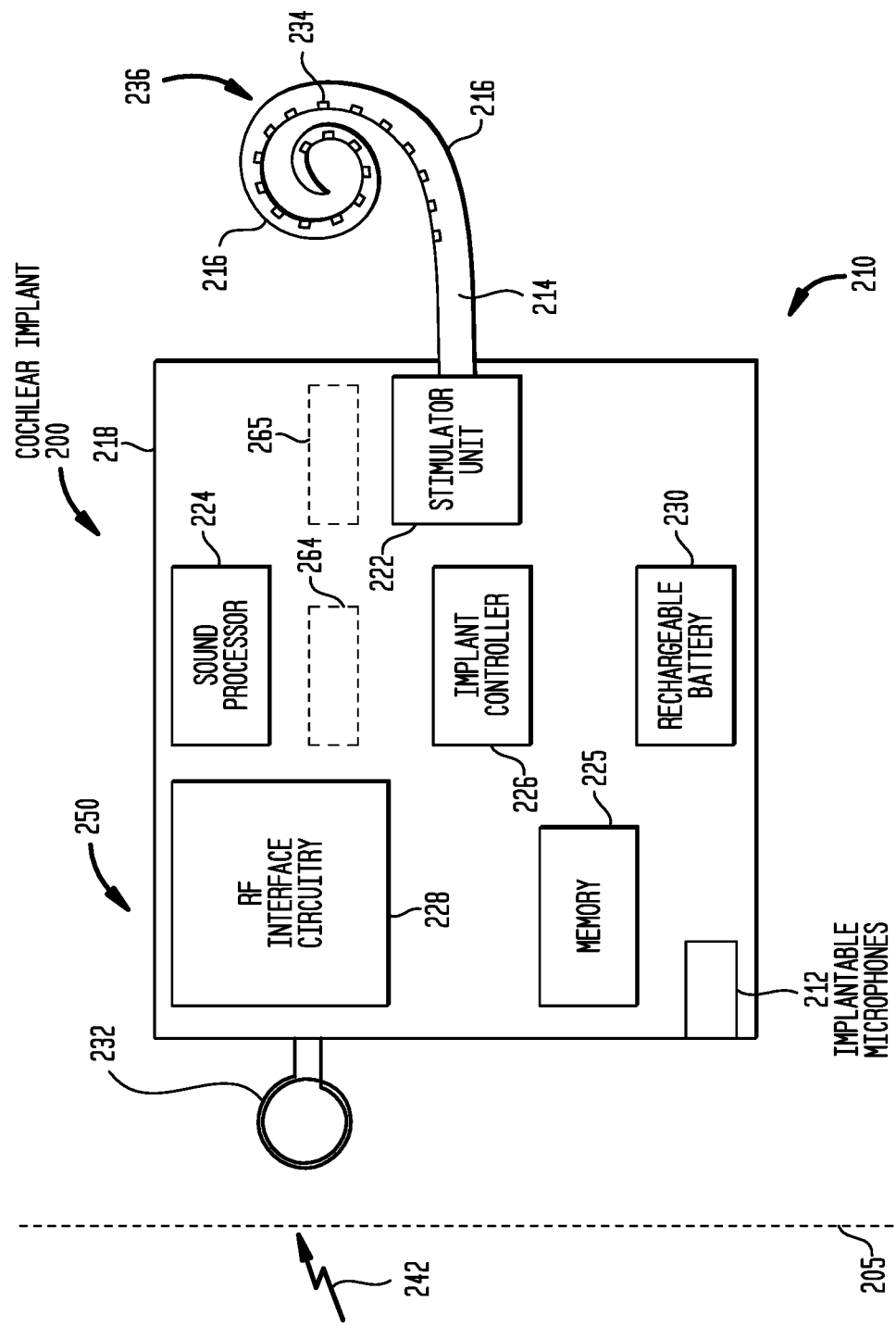
FIG. 2B is schematic block diagram of a cochlear implant, in accordance with certain embodiments presented herein.

It is to be appreciated that the cochlear implant 100 of FIG. 1, as well as the pillow charger 103 of FIG. 1, may each have a number of different arrangements. FIG. 2A is a block diagram illustrating one example arrangement for pillow charger 103, referred to as pillow charger 203, in accordance with embodiments presented herein. FIG. 2B is a block diagram illustrating one example arrangement for the cochlear implant 100, referred to as cochlear implant 200.

Referring first to FIG. 2A, the pillow charger 203 comprises a coil excitation system 248, sometimes referred to herein as a coil excitation system, and one or more coil antennas 250 that emit a magnetic field. For ease of description, pillow chargers in accordance with embodiments presented herein are primarily described with reference to the use of a single coil antenna. However, it is to be appreciated that pillow chargers in accordance with embodiments presented herein may include a plurality of coil antennas.

In the embodiment of FIG. 2B, the coil antenna 250 is formed by a plurality of "loops" or "coils" 252 of wire, where the plurality of loops are sometimes collectively referred as a "wire-loop bundle." The pillow charger 203 also comprises an electrical connection 254 to a power source. In one example, the electrical connection includes a galvanic isolation element or a transformer (not shown in FIG. 2A) to insulate the power source from the electronics of the pillow charger 203. The electrical connection 254 may also include a 12V DC adapter (not shown in FIG. 2A).

The coil excitation system 248 comprises one or more elements (e.g., a waveform generator, one or more amplifiers, tuning capacitors, etc.) that are used to drive the coil antenna 250 with an alternating current signal so that the coil antenna 250 will emit a corresponding magnetic field. That is, when driven by the coil excitation system 248, the wire coils 252 hold varying electrical currents that generate/emit magnetic fields that, as described further below, can be used to inductively charge the cochlear implant 200 (FIG. 2B).

Referring next to FIG. 2B, the cochlear implant 200 is a totally implantable cochlear implant where all components of the cochlear implant are configured to be implanted under the skin/tissue 205 of a recipient. Because all components are implantable, cochlear implant 200 operates, for at least a finite period of time, without the presence of an external device (e.g., without pillow charger 203).

Cochlear implant 200 includes an implant body (main module) 210, a lead region 214, and an elongate intra-cochlear stimulating assembly 216. The implant body 210 generally comprises a hermetically-sealed housing 218 in which a stimulator unit (stimulation electronics) 222, a sound processor 224, a memory 225, an implant controller 226 (i.e., battery and power management component or battery processor), RF interface circuitry 228, and a rechargeable battery 230 are disposed. It is to be appreciated that cochlear implant 200 may include one or more other components that, for ease of illustration, have been omitted from FIG. 2B.

The implant body 210 also includes one or more implantable sound inputs, such as microphones, accelerometers, etc. 212 and an internal/implantable coil 232 that are each typically located external to the housing 218. The implantable coil 232 is connected to elements within the housing 218 via hermetic feedthroughs (not shown in FIG. 2). Implantable coil 232 is typically a wire antenna coil comprised of multiple turns of electrically insulated single-strand or multi-strand platinum or gold wire. The electrical insulation of implantable coil 232 is provided by a flexible molding (e.g., silicone molding), which is not shown in FIG. 2A. Generally, a magnet is fixed relative to the implantable coil 232 for magnetic coupling with a magnet in an external device.

Elongate stimulating assembly 216 is configured to be at least partially implanted in the recipient's cochlea (not shown) and includes a plurality of longitudinally spaced intra-cochlear electrical stimulating contacts (electrodes) 234 that collectively form a contact array 236 for delivery of electrical stimulation (current) to the recipient's cochlea. Stimulating assembly 216 extends through an opening in the cochlea (e.g., cochleostomy, the round window, etc.) and has a proximal end connected to the stimulator unit 222 via the lead region 214 and a hermetic feedthrough (not shown in FIG. 2B). Lead region 214 includes one or more conductors (wires) that electrically couple the electrodes 234 to the stimulator unit 222. In this way, cochlear implant 200 electrically stimulates the recipient's auditory nerve cells, bypassing absent or defective hair cells that normally transduce acoustic vibrations into neural activity, in a manner that causes the recipient to perceive one or more components of the received sound signals.

The one or more implantable sound inputs 212 are configured to detect/receive input sound signals that are provided to the sound processor 224 by the RF interface circuitry 228. The sound processor 224 is configured to execute sound processing and coding to convert the received sound signals into output signals for use by the stimulator unit 222 in delivering electrical stimulation (current) to the recipient via electrodes 234.

The implantable coil 232 enables cochlear implant 200 to inductively receive power/current signals from a pillow charger (e.g., pillow charger 203) via an RF link, sometimes referred to herein as an inductive power link, which is represented in FIG. 2B by arrow 242. That is, as noted above with reference to FIG. 2A, when driven by the coil excitation system 248, the wire coils 252 of the coil antenna 250 hold varying electrical currents that generate/emit magnetic fields. When the implantable coil 232 is placed in proximity to the coil antenna 250 of the pillow charger 203 (FIG. 2A), the magnetic fields emitted by the coil antenna 250 pass through the implantable coil 232 and, as a result, a current is induced in the implantable coil 232. The RF interface circuitry 228 is configured to operate under the control of the implant controller 226 and contains the necessary switches so as to charge the rechargeable battery 230 using the power received via the inductive power link 242 (i.e., the rechargeable battery 232 is inductively charged by the pillow charger 202). The rechargeable battery 230 is configured to store sufficient energy needed to power the other elements of the cochlear implant 200, as well as to provide the current needed to electrically stimulate the recipient's cochlea.

The total amount of energy a battery can store at any one time, often measured in terms of Milliampere Hours (mAh), is referred to herein as the "capacity" of the battery. It is generally assumed that a recipient has the ability to charge his/her rechargeable battery at night and, as such, the goal is to provide a recipient with approximately one full day of operation on a single battery charge (i.e., a fully charged battery should power the cochlear implant for at least approximately 14-16 hours without the need to recharge the battery). As such, pillow charger 203 is a device that is used to inductively charge rechargeable battery 230 while the recipient is asleep (e.g., during the night). In accordance with embodiments presented herein, the typical use of night-time chargers, such as pillow charger 203, while a recipient is asleep is leveraged to activate a secondary mode of operation of a cochlear implant, sometimes referred to herein as a "night-time" mode.

More specifically, in the embodiment of FIG. 2B, the implant controller 226 is configured to detect inductive charging of the rechargeable battery 230 (e.g., detect the initiation/beginning of a battery charging cycle). In response to detecting the inductive charging, the implant controller 226 is configured to switch the cochlear implant 200 to a night-time mode of operation. As such, in accordance with embodiments presented herein, the cochlear implant 200 has at least two distinct modes of operation, namely a "primary" mode of operation that is activated when the cochlear implant 200 is not being charged by pillow charger 203 and the secondary or "night-time" mode of operation that is only activated in response to detection of inductive charging of the rechargeable battery 230 by pillow charger 203. Although the secondary mode of operation of cochlear implant 200 is described as being a "night-time" mode, it is to be appreciated that this mode may also or alternatively be activated at different times of the day. In general, the "night-mode" is used to refer to a mode of operation that is triggered when the rechargeable battery 230 is being inductive charged by the pillow charger 203.

In the primary mode of operation, the implant controller 226 causes the cochlear implant 200 to operate in accordance with a first set of settings (e.g., clinically determined settings) that enable the cochlear implant to detect acoustic sound signals and to evoke perception of those acoustic sound signals. In contrast, in the night-mode of operation of the cochlear implant 200, the implant controller 226 causes the cochlear implant 200 to operate in accordance with a second set of settings that are specifically tailored to a sleeping recipient (e.g., reduce power consumption and/or to provide extra functionality/therapy that is useful at night like tinnitus suppression signals, fire alarm detection, wake-up signals, sleep inducing sounds, etc.)

The second set of settings that are activated during the night-mode of operation may be take a number of different forms. In one embodiment, the second set of settings form a "reduced-sensitivity sound processing program" in which the cochlear implant 200 intentionally eliminates/omits, from delivery to the recipient, sounds with certain attributes so as to minimize disturbances to the recipient while the recipient is sleeping. That is, while executing the reduced-sensitivity sound processing program, the cochlear implant 200 processes sounds in a manner that intentionally reduces the functionality of the implant. This type of operation is different from the processing that is executed in the primary mode of operation where, in general, the cochlear implant 200 attempts to maximize sound understanding (i.e., the cochlear implant 200 processes the signals coming from the implantable microphone and turns this into stimulation pulses inside the cochlea to provide speech understanding).

For example, in accordance with one reduced-sensitivity sound processing program, the sound processor 224 is configured to prevent, from being delivered to the recipient, acoustic sounds that have an amplitude that is below a predetermined threshold level. This may be implemented by raising an acoustic hearing threshold that is used by the sound processor 224 during the night-time mode relative to an acoustic hearing threshold using during the primary mode (i.e., the implant controller 226 increasing the minimum acoustic amplitude that is needed to trigger delivery of stimulation to the recipient).

In the same or other reduced-sensitivity sound processing program, the sound processor 224 is also or alternatively configured to prevent, from being delivered to the recipient, acoustic sounds that have an amplitude that is above a predetermined comfort level. This may be implemented by dropping any sound signals that have an acoustic amplitude greater than a predetermined upper threshold level.

In certain such embodiments, the determination of whether to drop sound signals that exceed the predetermined upper threshold level is accompanied by a secondary determination relating to temporal aspects of the sound. That is, the sound processor 224 may be configured to prevent acoustic sounds from being delivered to the recipient only when: (1) the acoustic amplitude is greater than the predetermined upper level, and (2) when the acoustic sounds are associated with predetermined temporal characteristics. For example, the sound processor 224 may eliminate high amplitude acoustic sounds that also have a time length that is less than a predetermined threshold, are not repeated within a predetermined time period, etc. The sound processor 224 may also be configured to monitor for key danger words (e.g., "FIRE," "HELP," "MOM," "DAD," etc.) and allow those sounds to be delivered to the recipient regardless of the sound level, temporal characteristics, etc.

In another embodiment, the second set of settings form a "reduced-power consumption sound processing program" in which the implant controller 226 intentionally reduces the functionality of the cochlear implant 200 to conserve power. That is, the cochlear implant 200 generally operates differently from that implemented in the primary mode of operation in a manner that intentionally reduces the functionality of the implant. More specifically, in certain reduced-power consumption sound processing programs the implant controller 226 is configured to reduce the number/amount of current pulses that are stimulated inside the cochlea. For example, where a typical primary (day-time) program might stimulate the cochlea at a certain rate (e.g., 7000 pulses per second), a reduced-power consumption sound processing program might reduce the stimulation rate to predetermined upper limit (e.g., 3500 pulses per second). In certain examples, stimulation pulses may be delivered up to the upper limit and only started again when needed (e.g., during a fire alarm).

In other reduced-power consumption sound processing programs the implant controller 226 is configured to reduce the clock rate used by the sound processor 224. For example, where a typical primary (day-time) program may run on a 20 MHz clock, a reduced-power consumption sound processing program might reduce the clock to 10 MHz or 5 MHz at night.

Another alternative for a reduced-power consumption sound processing program is to disable certain elements of the cochlear implant 200. For example, the sound processor 224 may be formed by a plurality (e.g., 6) Digital Signal Processors (DSPs) which all may be simultaneously enabled during a typical primary (day-time) program. During a reduced-power consumption sound processing program, several of the DSPs could be disabled and only activated if/when needed.

In another embodiment, the second set of settings include a "tinnitus masking program" in which tinnitus masking signals are delivered to the recipient. For example, in accordance with one illustrative tinnitus masking program, the implant controller 226 is configured to initiate the delivery of tinnitus masking signals to the recipient for at least a period of time (e.g., a predetermined period of time). The tinnitus masking signals can have different shapes and forms (e.g., a pure sine at a certain frequency, the sound of the sea, white noise, music, etc.). In general, a tinnitus masker may be a "tone-generator" inside sound processor 224, a prerecorded sample that is read from memory 225, etc.

In certain tinnitus masking programs, the tinnitus masking signals may be delivered to the recipient continuously/periodically the entire time that the cochlear implant 200 operations in the night-time mode. In other tinnitus masking programs, the tinnitus masking signals may only be delivered for limited periods of time (e.g., 1 hour, 2 hours, etc.). For example, tinnitus may be most problematic while the recipient is attempting to fall asleep. As such, the tinnitus masking signals may be delivered for a time period that is sufficient for the recipient to fall asleep and, thereafter, the tinnitus masking signals are no longer delivered (e.g., to reduce power consumption). In still other tinnitus masking programs, the tinnitus masking signals may be delivered until the implant controller 226 determines that the recipient has fallen asleep. This determination may be made based on, for example, inputs from an implantable accelerometer or other sensor.

As noted, in certain embodiments, the sound processor 224 uses a tinnitus mask stored in the memory 225 to generate the tinnitus masking signals. In other embodiments, the tinnitus masking signals are generated in real-time by the sound processor 224 (i.e., a tone generator as part of a DSP). In one such embodiment, the sound processor 224 uses the time-varying current in the implantable coil 232 is used to at least partially or pseudo-randomize the tinnitus masking signal. This could be implemented in a number of manners, such as using the least significant bit) (LSB) of the incoming signal, etc.

In certain embodiments, the parameters utilized in a selected night-time mode are stored in memory 225. However, in other embodiments, the pillow charger 203 can communicate some parameters (e.g., via load modulation or a separate data link) to the cochlear implant 200.

As noted above, the implant controller 226 is configured to initiate the night-time mode in response to detecting inductive charging of the rechargeable battery 230 by the pillow charger 203. The implant controller 226 can be configured to detect the inductive charging in a number of different manners.

Figure 3:
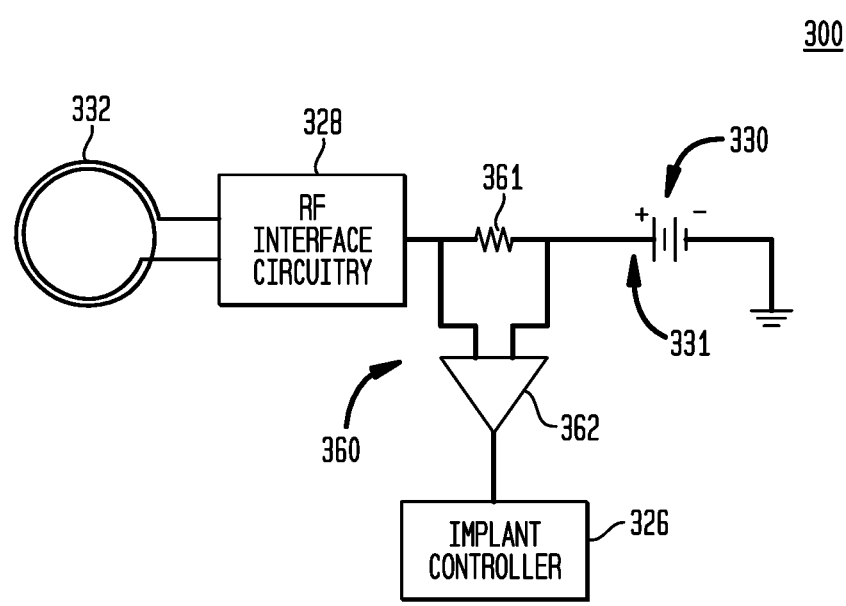
FIG. 3 is a schematic diagram of a portion of a cochlear implant, in accordance with certain embodiments presented herein.

In one embodiment, the implant controller 226 is configured to detect the inductive charging of the rechargeable battery 230 based on the current that is supplied to the rechargeable battery. FIG. 3 is a simplified schematic diagram illustrating one such arrangement where a cochlear implant 300 includes, among other elements, an implantable coil 332, RF interface circuitry 328, a rechargeable battery 330, and an implant controller 326, all of which may be implemented as described above with reference to FIG. 2B. For ease of illustration, other elements of the cochlear implant 300 have been omitted from FIG. 3.

In the example of FIG. 3, a current sense circuit 360 is located between the RF interface circuitry 328 and the input (positive terminal) 331 of the rechargeable battery 330. In this illustrative embodiment, the current sense circuit 360 comprises a sense resistor 361 and an amplifier 362. In general, the current sense circuit 360 provides the implant controller 326 with an input (e.g., measurement) indicating, for example, the level/magnitude of the current that is provided to the rechargeable battery 330 (i.e., a measure of the instantaneous charging current for the battery). Based on the input (e.g., current measurement), the implant controller 326 can determine when charging of the rechargeable battery 330 has been, for example, initiated, completed, etc. For example, the implant controller 326 may detect when the current that is provided to the rechargeable battery 330 increases (e.g., above a predetermined threshold), indicating that the rechargeable battery 330 is receiving a charging current from a pillow charger charger. As a result, the implant controller 326 can initiate a night-time mode of operation, as described above.

It is to be appreciated the current sense circuit 360 of FIG. 3 is illustrative and that other implementations for current sense circuits or for detecting inductive charging of the rechargeable battery based on the current that is supplied to the rechargeable battery are within the scope of the present invention. It is also to be appreciated that an implantable medical device in accordance with embodiments presented herein may detect inductive charging of a rechargeable battery using other techniques.

For example, returning to the specific arrangements of FIGS. 2A and 2B, the implant controller 226 may be configured to detect inductive charging of the rechargeable battery 230 using information obtained from the inductive power link 242. The coil antenna 250 (FIG. 2A) of the pillow charger 203 and the implantable coil 232 are closely coupled to one another and the coil antenna 250 transmits a continuous time-varying RF carrier signal (i.e., wave). That is, a continuous time-varying RF carrier signal forms a basis of the inductive power link 242 and is used to transfer power to the cochlear implant 200. In accordance with certain embodiments presented herein, the pillow charger 203 is configured to use this inductive coupling to signal to the cochlear implant 200 that charging of the rechargeable battery 230 is going to be, and/or has been, initiated.

More specifically, in one such example, the pillow charger 203 is configured to alter/adjust one or more characteristics of the coil excitation system 248 in accordance with a predetermined pattern/sequence which, due to the coupling between the coil antenna 250 and the implantable coil 232, causes a corresponding predetermined pattern/sequence of impedance changes (referred sometimes as reflected load) at the implantable coil 232 (e.g., change of the load at the implantable coil 232 sensed by an implantable coil impedance sensor). This impedance/load change sensed at the implantable coil 232 affects the amount of current flowing through the implantable coil 232 and the sequence of load changes is detectable via current changes at the implantable coil 232.

Detection of the predetermined pattern/sequence of impedance changes at the implantable coil 232 signals to the implant controller 226 the initiation of charging of the rechargeable battery 230 (i.e., that a battery charging cycle is beginning or is about to begin). As a result, when the predetermined pattern/sequence of impedance changes is detected, the implant controller 226 can initiate a night-time mode of operation, as described above.

As noted above, in certain embodiments presented herein the pillow charger 203 can utilize load modulation of the inductive power link 242 to signal to the implant controller 226 the initiation of charging of the rechargeable battery 230. In other embodiments, the pillow charger 203 can utilize on-off keying to signal the initiation of charging of the rechargeable battery 230. More specifically, when initiation charging, the pillow charger 203 could turn the time-varying RF carrier signal on and off in accordance with a predetermined sequence/pattern (e.g., alternatively turn the RF carrier signal on five times and off five times). This on-off keying sequence is detectable by a sensor in the cochlear implant 200. As a result, when the predetermined on-off keying sequence is detected, the implant controller 226 can initiate a night-time mode of operation, as described above.

In further embodiments, the implant controller 226 may determine that charging of the rechargeable battery 230 has been initiated based on a voltage measured at the implantable coil 232. For example, in certain embodiments the pillow charger 203 may induce a characteristic voltage and/or a characteristic voltage pattern at the implantable coil 232 when providing charging power to the cochlear implant. When the characteristic voltage and/or a characteristic voltage pattern at is detected by the implant controller 226 (e.g., via a sensor coupled to the implantable coil 232), the implant controller 226 can initiate a night-time mode of operation, as described above. The characteristic voltage and/or a characteristic voltage pattern can take a number of different forms. In one example, the pattern could be 100 ms on, 100 ms off, 200 ms on, 200 ms off, 100 ms on, 100 ms off. Further examples of characteristic voltage and/or a characteristic voltage patterns generated by a pillow charger, and which may be detected at an implantable coil and implant controller, are described in commonly-owned and co-pending U.S. patent application Ser. No. 15/454,405, filed on Mar. 9, 2017, the content of which is hereby incorporated by reference herein.

In certain embodiments, cochlear implant 200 is coupled to a pillow charger that includes multiple coil antennas each configured to emit a magnetic field. In these embodiments, the pillow charger is configured to shift the phase, amplitude, and/or other characteristics of one or more of the emitted magnetic fields. By varying at least one characteristic of the emitted magnetic fields relative to one another (i.e., varying the relative phase and/or relative amplitude differences between the emitted magnetic fields), the direction/orientation of the combined magnetic field vector also changes (e.g., rotates) over time. As a result, regardless of the relative locations of the multiple coil antennas and the implantable coil 232, the implantable coil 232 will, at different times, have different amounts of magnetic flux there through that induces a current in the implantable coil. In these embodiments, the variation in the magnetic flux through the implantable coil 232 is detected by the implant controller 226 (e.g., via a sensor coupled to the implantable coil 232), and the implant controller 226 can initiate a night-time mode of operation, as described above.

FIG. 2B illustrates an example sensor 264 that may be included in cochlear implant 200 to monitor one or more characteristics of the inductive power link 242 and/or the implantable coil 232 (e.g., load changes, on-off keying, voltage, etc.) for use by the implant controller 226. The sensor 264 is shown using dashed lines to indicate that the use of the sensor 264 is illustrative of the embodiments described above.

In the above embodiments, no additional communication between the pillow charger 203 and the cochlear implant 200, beyond the inductive power link 242, is needed for the implant controller 226 to detect initiation of charging of the rechargeable battery 230 (i.e. the pillow charger 203 operates in an "open-loop" configuration without feedback from the cochlear implant). However, in certain arrangements, the cochlear implant 200 and the pillow charger 203 cane be configured to communicate with one another via a separate data link. For example, the cochlear implant 200 and the pillow charger 203 may each be configured with a wireless short range transceiver (e.g., a Bluetooth® transceiver, a Bluetooth® Low Energy (BLE) transceiver, etc.) for direct communication with one another. Bluetooth® is a registered trademark owned by Bluetooth SIG, Inc. That is, a separate communication/data link may be provided between the cochlear implant 200 and the pillow charger 203 (i.e., running in parallel with the inductive power link 242) and this separate data link can be used by the pillow charger 203 to inform the cochlear implant 200 that charging of the rechargeable battery 230 has been, or is going to be, initiated.

Figure 4:
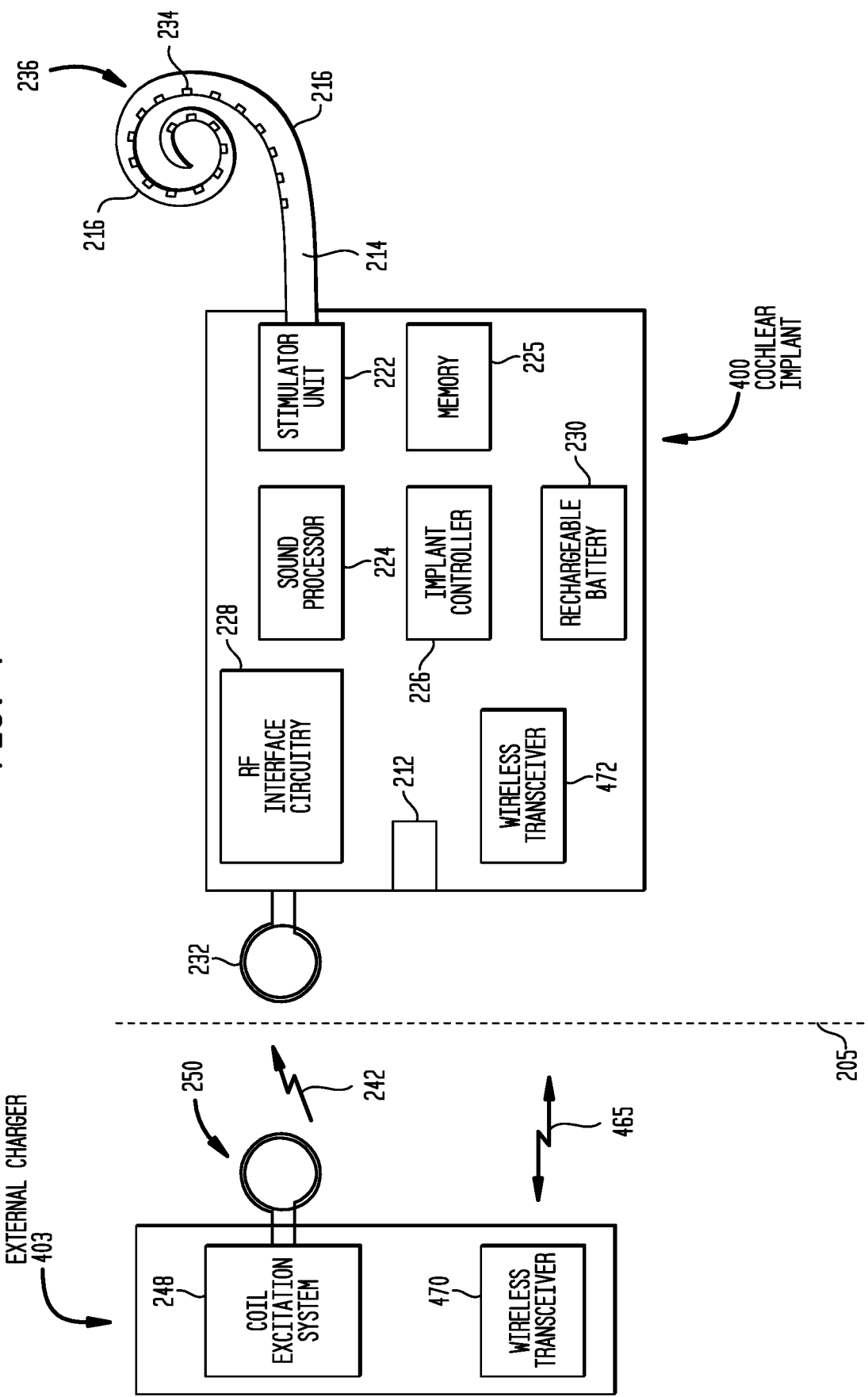
FIG. 4 is schematic block diagram of a cochlear implant, in accordance with certain embodiments presented herein.

FIG. 4 is a simplified block diagram of a pillow charger 403 and a cochlear implant 400 configured to communicate with one another via the inductive power link 242 and a separate wireless data link 465. Pillow charger 403 is similar to pillow charger 203 of FIG. 2A and comprises the coil excitation system 248 and the coil antenna 250. Pillow charger 403 also comprises a wireless transceiver 470.

Cochlear implant 400 is similar to cochlear implant 200 of FIG. 2B and comprises the implantable sound inputs(s) 212, the sound processor 224, the implantable coil 232, the memory 225, the implant controller 226, the RF interface circuitry 228, the rechargeable battery 230, the stimulator unit 222, the implant controller 226, and the stimulating assembly 236. Cochlear implant 400 also comprises a wireless transceiver 472.

The wireless transceivers 470 and 472 are each configured in accordance with one or more wireless technology standards and are configured to exchange data over a short distance (e.g., using short-wavelength Ultra high frequency (UHF) radio waves in one or more industrial, scientific and medical (ISM) radio bands, such as the ISM band from 2.4 to 2.485 GHz). That is, the wireless transceivers 470 and 472 provide the wireless data link 465.

Embodiments have generally been described above with reference to different primary (single factor) determinations for detection of pillow charging operations (i.e., for detecting the charging of an implantable rechargeable battery). It is to be appreciated that certain embodiments presented herein may combine the above determinations to detect inductive charging of an implantable rechargeable battery. That is, it is to be appreciated that the different determinations described above are illustrative and that other determinations may be used in accordance with embodiments presented herein. It is also to be appreciated that the above determinations are not mutually exclusive and that multiple determinations may be used together.

It is also to be appreciated that certain embodiments presented herein may also make use one or more additional "secondary" inputs to confirm that the cochlear implant is coupled to a night-time charger and, accordingly, to confirm whether the night-time mode of operation should be initiated. In certain examples, these secondary inputs may do not relate to whether the rechargeable battery is being charged, but instead relate to ancillary factors. The secondary inputs are used to ensure that the night-time mode is not initiated when the cochlear implant is receiving charging power from another type of external charger, such as a body worn charger, a chair-based charger, etc. For ease of illustration, secondary inputs for use in confirming whether the night-time mode should be initiated are described with reference to the arrangements of FIGS. 2A and 2B and are combined with one or more of the other determinations for detection of pillow charging operations described elsewhere herein.

In one embodiment, the secondary input used to determine whether the night-time mode should be initiated is the time that has elapsed since the last battery charging cycle (e.g., the time since the most recent previous battery charging cycle was initiated, the time since the most recent previous battery charging cycle ended, etc.). As noted above, a night-time charger, such as pillow charger 203, is generally used each night while the recipient is asleep. As a result, the relative timing between the most recent charging cycles could be used by the implant controller 226 to differentiate between different types of chargers, reflected in the relative usage timings. For example, detection of a new charging cycle 20-24 hours after the beginning of the most recent previous pillow charger-based charging cycle may indicate that the battery is one again being charged by the pillow charger 203.

In these embodiments, the implant controller 226 is configured to track the timing of charging cycles (e.g., via an embedded timer). In certain embodiments, the relative timing between charging cycles may be analyzed in view of the current time-of-day (ToD) to differentiate between different types of chargers and, accordingly, to confirm whether the night-time mode of operation should be initiated. In other embodiments, the secondary input used to determine whether the night-time mode should be initiated is the time-of-day only (i.e., without reliance on the relative timing between the most recent charging cycles).

In another embodiment, the secondary input used to determine whether the night-time mode of operation should be initiated is the acoustic scene/environment. In these embodiments, the sound processor 224 or the implant controller 226 is configured to evaluate/analyze received sound signals to determine the primary or main sound "class" of the sound signals (i.e., determine the environment in which the cochlear implant is currently/presently located). That is, the sound processor 224 or the implant controller 226 is configured to use the received sound signals to "classify" the ambient sound environment of the cochlear implant 200 and/or the sound signals into one or more sound categories (i.e., determine the input signal type). The sound classes/categories may include, but are not limited to, "Speech," "Noise," "Speech+Noise," "Music," and "Quiet." Using the determined class, the implant controller 226 is configured to determine whether the rechargeable battery 230 is receiving power from pillow charger 203 or some other type of charger and accordingly, to confirm whether the night-time mode of operation should be initiated.

For example, if the rechargeable battery 230 is receiving power and it is determined that the cochlear implant 200 is in a "Noise" environment, then the implant controller 226 may determine that the implant rechargeable battery 230 is receiving power from a charger other than the pillow charger 203 (e.g., the recipient is watching television and is receiving power from a chair-based charger). As a result, it may be undesirable to activate the night-time mode. Conversely, if the rechargeable battery 230 is receiving power and it is determined that the cochlear implant 200 is in a "Quiet" environment, then the implant controller 226 may determine that the implant rechargeable battery 230 is in receiving power from the pillow charger 203. As such, the implant controller 226 may initiate the night-time mode.

In another embodiment, the secondary input used to determine whether the night-time mode of operation should be initiated is the output of an accelerometer or other sensor that is used to track, for example, the orientation of the recipient's head. Using the input from this type of sensor, the implant controller 226 could determine whether the recipient is laying down and, as such, likely receiving power from a night-time charger. FIG. 2B illustrates an example accelerometer 265 that may be included in cochlear implant 200. The accelerometer 265 is shown using dashed lines to indicate that the use of accelerometer 265 is illustrative of the embodiments described above.

In a further embodiment, the cochlear implant 200 is configured to monitor, for example, the recipient's heartrate, breathing rate, etc. and these attributes may be used as the secondary input used. In certain examples, the recipient's heartrate, breathing rate, etc. could be tracked using the implantable sound inputs 212 and analyzed to determine when the recipient is likely falling asleep and, as such, when the night-time mode should be activated.

It is to be appreciated that the different secondary inputs described above are illustrative and that other secondary inputs may be used in accordance with embodiments presented herein. It is also to be appreciated that the secondary inputs are not mutually exclusive and that multiple secondary inputs may be used together to confirm whether the night-time mode should be initiated.

Figure 5:
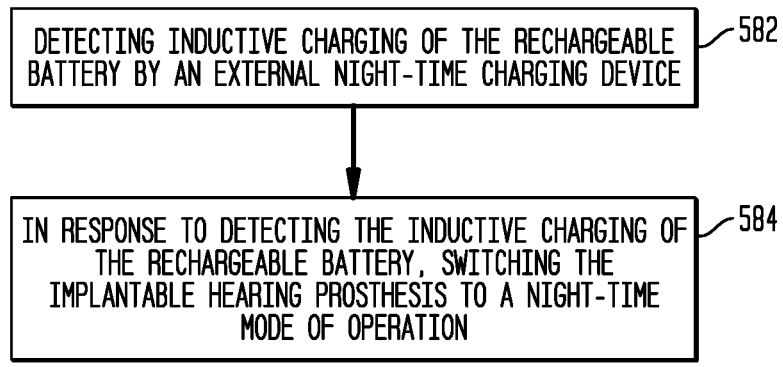
FIG. 5 is a flowchart of a method, in accordance with certain embodiments presented herein.

FIG. 5 is a flowchart of a method 580 performed at an implantable hearing prosthesis comprising a rechargeable battery, in accordance with embodiments presented herein. Method 580 begins at 582 where the implantable hearing prosthesis detects inductive charging of the rechargeable battery by an external night-time charging device. At 584, in response to detecting the inductive charging, the implantable hearing prosthesis is switched to a night-time mode of operation. In one embodiment, switching to the night-time mode of operation includes delivery of tinnitus masking signals to the recipient for at least a period of time. In the same or other embodiments, switching to the night-time mode of operation includes initiating a reduced-sensitivity sound processing program. In the same or other embodiments, switching to the night-time mode of operation includes initiating a reduced-power consumption sound processing program.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
    at an implantable medical device comprising a rechargeable battery and an implantable coil:
        receiving, via the implantable coil, inductive charging signals transmitted by an external coil of an external night-time charging device to the implantable coil via an inductive link;
        determining, based on the inductive charging signals received at the implantable coil, that the rechargeable battery is being inductively charged by the external night-time charging device via the inductive charging signals; and
        in response to determining that the rechargeable battery is being inductively charged, switching the implantable medical device to a night-time mode of operation.

2. The method of claim 1, wherein determining, based on the inductive charging signals received at the implantable coil, that the rechargeable battery is receiving power from being charged by an external night-time charging device comprises:

monitoring current provided from the implantable coil to the rechargeable battery to detect the beginning of a battery charging cycle.

3. The method of claim 1, wherein determining, based on the inductive charging signals received at the implantable coil, that the rechargeable battery is being inductively charged by the external night-time charging device comprises:
   detecting, at the implantable medical device, a predetermined pattern of load modulation of the inductive link.

4. The method of claim 1, wherein determining, based on the inductive charging signals received at the implantable coil, that the rechargeable battery is being inductively charged by the external night-time charging device comprises:
   detecting, at the implantable medical device, a predetermined on-off keying pattern of the inductive link.

5. The method of claim 1, wherein determining, based on the inductive charging signals received at the implantable coil, that the rechargeable battery is being inductively charged by the external night-time charging device comprises:
   detecting, at the implantable medical device, a predetermined voltage pattern at the implantable coil.

6. The method of claim 1, further comprising:
   receiving, via a secondary wireless communication link, a charging initiation notification from the external night-time charging device.

7. The method of claim 1, wherein switching the implantable medical device to a night-time mode of operation comprises:
   delivering tinnitus masking signals to a recipient of the implantable medical device for at least a period of time.

8. The method of claim 7, wherein the inductive link uses a magnetic field to induce time-varying current in the implantable coil, and wherein the method further comprises:
   using the time-varying current in the implantable coil to at least partially randomize the tinnitus masking signals.

9. The method of claim 1, wherein switching the implantable medical device to a night-time mode of operation comprises:
   initiating a reduced-sensitivity processing program.

10. The method of claim 1, wherein switching the implantable medical device to a night-time mode of operation comprises:
    initiating a reduced-power consumption processing program.

11. The method of claim 1, wherein determining that the rechargeable battery is being inductively charged by the external night-time charging device comprises:
    confirming, based on one or more secondary inputs, that the inductive charging is initiated by the external night-time charging device.

12. The method of claim 11, wherein the one or more secondary inputs comprise at least one of a time-of-day or a relative period of time since a previous battery charging cycle.

13. The method of claim 11, wherein the one or more secondary inputs comprise a determined sound class of the ambient sound environment of the medical device.

14. An implantable component, comprising:
    an implantable coil configured to be inductively coupled to an external coil of an external night-time charging device to form an inductive link over which the implantable coil receives inductive charging signals;
    an implantable rechargeable battery; and
    an implant controller configured to determine, based on the inductive charging signals received at the implantable coil, that the rechargeable battery is being inductively charged by the inductive charging signals received from the external night-time charging device, and, in response to determining that the rechargeable battery is being inductively charged via the inductive charging signals, initiate a night-time mode of operation for the implantable component.

15. The implantable component of claim 14, further comprising:
    a current sense circuit configured to monitor current provided to the rechargeable battery and to generate an output representative of the current,
    wherein the implant controller is configured to determine, based on the output of the current sense circuit, a beginning of a battery charging cycle.

16. The implantable component of claim 14, wherein to determine, based on the inductive charging signals received at the implantable coil, that the rechargeable battery is being inductively charged by the inductive charging signals received from the external night-time charging device, the implant controller is configured to:
    monitor the inductive link for a predetermined load modulation pattern indicating initiation of a battery charging cycle.

17. The implantable component of claim 14, wherein to determine, based on the inductive charging signals received at the implantable coil, that the rechargeable battery is being inductively charged by the inductive charging signals received from the external night-time charging device, the implant controller is configured to:
    monitor the inductive link for a predetermined on-off keying pattern indicating initiation of a battery charging cycle.

18. The implantable component of claim 14, wherein to determine, based on the inductive charging signals received at the implantable coil, that the rechargeable battery is being inductively charged the inductive charging signals received from the external night-time charging device, the implant controller is configured to:
    monitor the inductive link for a predetermined voltage pattern indicating initiation of a battery charging cycle.

19. The implantable component of claim 14, further comprising:
    a wireless transceiver configured to receive notifications from the external night-time charging device.

20. The implantable component of claim 14, wherein to initiate a night-time mode of operation for the implantable component, the implant controller is configured to:
    initiate delivery of tinnitus masking signals to a recipient of the implantable component for at least a period of time.

21. The implantable component of claim 14, wherein to initiate a night-time mode of operation for the implantable component, the implant controller is configured to:
    initiate a reduced-sensitivity processing program.

22. The implantable component of claim 14, wherein to initiate a night-time mode of operation for the implantable component, the implant controller is configured to:
    initiate a reduced-power consumption processing program.

23. The implantable component of claim 14, wherein prior to initiating the night-time mode of operation, the implant controller is configured to confirm, based on one or more secondary inputs, that the rechargeable battery is being inductively charged by the external night-time charging device.

24. The implantable component of claim 23, wherein the one or more secondary inputs comprise at least one of a time-of-day or a relative period of time since a previous battery charging cycle.

25. The implantable component of claim 23, wherein the one or more secondary inputs comprise a determined sound class of the ambient sound environment of the component.

* * * * *